United States Patent [19]

Warriner

[11] Plant 5,152

[45] Dec. 6, 1983

[54] ROSE PLANT JACGUM

[75] Inventor: William A. Warriner, Tustin, Calif.

[73] Assignee: Jackson & Perkins Company, Medford, Oreg.

[21] Appl. No.: 353,023

[22] Filed: Mar. 1, 1982

[51] Int. Cl.[3] ..... A01H 5/00

[52] U.S. Cl. ..... Plt./10

[58] Field of Search ..... Plt./10

*Primary Examiner*—Robert E. Bagwill

*Attorney, Agent, or Firm*—Klarquist, Sparkman, Campbell, Leigh, Whinston & Dellett

[57] ABSTRACT

A miniature rose variety having a low, well branched, spreading plant; small foliage; abundant blooms in clusters; and deep red color.

1 Drawing Figure

This present invention relates to a new and distinct variety of rose plant of the miniature class which was originated by me by crossing two unnamed varieties.

The primary objective of this breeding was to produce a new rose variety of dense habit, clean foliage, and abundant red blooms. This objective was substantially achieved along with other desirable improvements as evidenced by the following unique combination of characteristics which are outstanding in the new variety and which distinguish it from its parents, as well as from all other varieties of which I am aware:

1. A low, well branched, spreading plant.
2. Small, clean foliage.
3. Abundant blooms in clusters.
4. Deep red color which fades very little.

Asexual reproduction of this new variety by cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Unnamed variety.

*Pollen parent.*—Unnamed variety.

Classification:

*Botanical.*—Rosa hybrid.

*Commercial.*—Miniature.

FLOWER

Observations made from specimens grown at Irvine, Calif. in November.

Blooming habit: Continuous.

Bud:

*Size.*—1" to 1¼" when petals start to unfurl.

*Form.*—Pointed ovoid.

*Color.*—When sepals first divide, Red 46A. When half blown, upper side of petals Red 46A; lower side of petals Red 46C.

*Sepals.*—Color: Outer surface Green 138A, smooth surface. Three appendaged sepals lightly appendaged. Two unappendaged sepals hairy edged.

*Receptacle.*—Color: Green 138A. Shape: Funnel. Size: Large. Surface: Smooth.

*Peduncle.*—Length: Short. Surface: Glandular. Color: Light green. Strength: Stiff, erect.

*Opening.*—Spiral type in tight bud; petals remain perpendicular to stem when fully expanded.

Bloom:

*Size.*—Small. Average open size is 1½ inches.

*Borne.*—In clusters; flat.

*Stems.*—Short, strong.

*Form.*—When first open, flat. Permanence: Retains its form to the end.

*Petalage.*—Number of petals under normal conditions: 75-80.

*Color.*—Center of flower: Upper side of petals Red 46A; reverse side of petals Red 46C; base of petals white. General tonality from a distance Red 46C.

*Variegations.*—Occasional vegetative streak on outer petals.

*Discoloration.*—General tonality at end of first day: No change is noticed until blooms are open 4 to 5 days, then only slight fading.

*Fragrance.*—None.

Petals:

*Texture.*—Thin.

*Shape.*—Obovate.

*Form.*—Heavily quilled.

*Arrangement.*—Imbricated. Petaloids in center, few.

*Persistence.*—Drop off cleanly.

*Lastingness.*—On the plant, long. As cut flower, long.

Reproductive parts:

*Anthers.*—Small, many. Color: Yellow. Arrangement: Regular around styles.

*Filaments.*—Color: Yellow.

*Pollen.*—Lemon yellow. Very little pollen.

*Styles.*—Color: Light green.

*Stigmas.*—Color: Yellow.

PLANT

Form: Bush.

Growth: Vigorous, dwarf, branching, reaches 20" height in first year.

Foliage: Number of leaflets on normal mid-stem leaves: 5 or 7.

*Size.*—Small.

*Quantity.*—Normal.

*Color.*—New foliage: Greyed Purple 183A. Old foliage: Green 136B.

Leaflets:

*Shape.*—Oval pointed.

*Texture.*—Leathery on upper side.

*Edge.*—Serrated.

*Serration.*—Single, small.

*Petiole.*—Rachis: Color: Reddish. Underside: Prickles.

*Stipules.*—Long, bearded.

*Disease resistance.*—Resistant to mildew under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, ordinary. On laterals from stalk, ordinary.

*Form.*—Long, hooked slightly downward.

*Color when young.*—Brown.

*Position.*—Irregular.

Small prickles:

*Quantity.*—On main stalks, none. On laterals, none.

I claim:

1. A new and distinct variety of rose plant of the miniature class, substantially as herein shown and described, characterized particularly as to novelty by the unique combination of its abundant red buds and blooms borne on a low, dense plant with small disease resistant foliage.

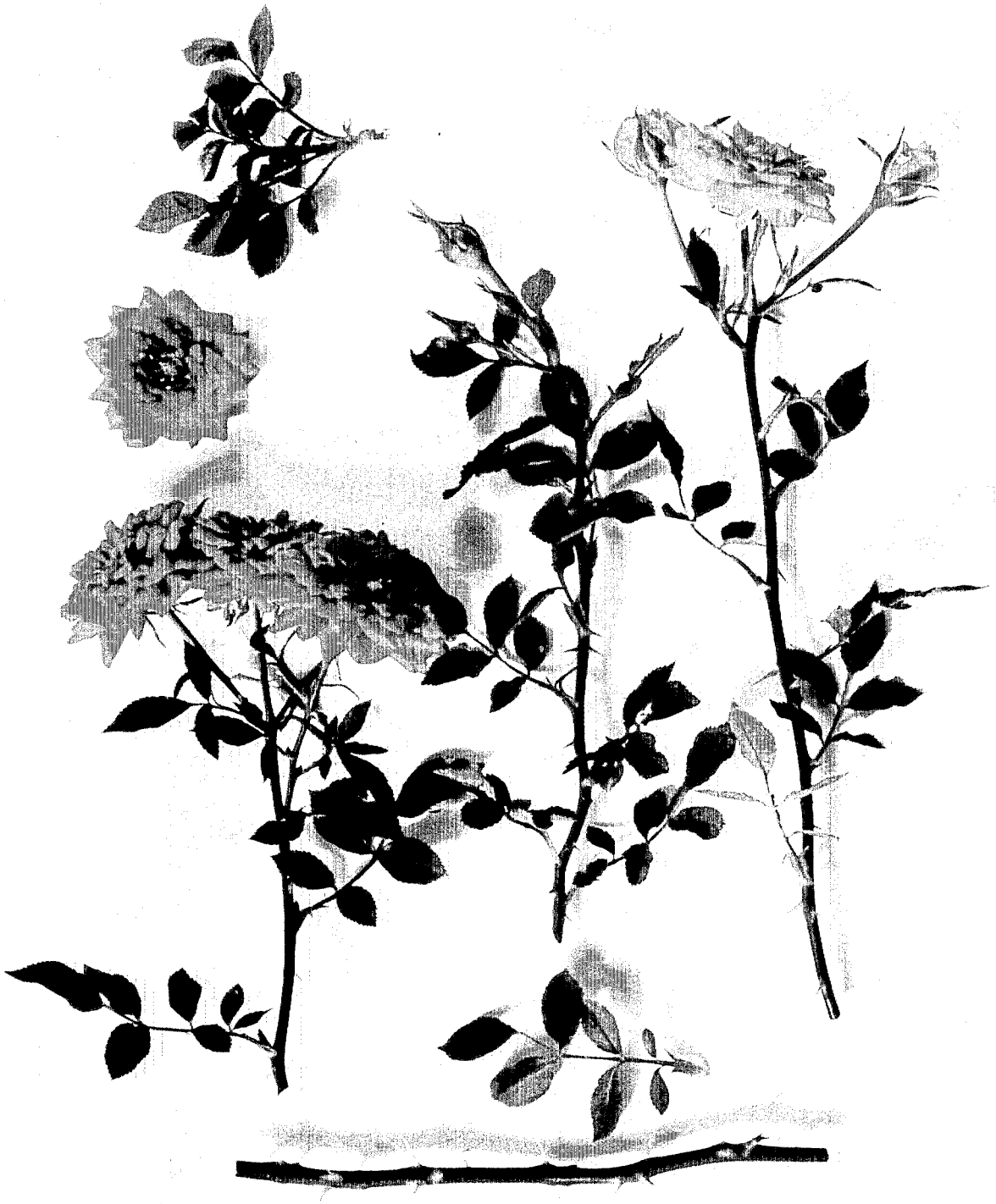

* * * * *